United States Patent
Menta et al.

(10) Patent No.: US 6,987,122 B2
(45) Date of Patent: Jan. 17, 2006

(54) 2-(1H-INDOL-3-YL)-2-OXO-ACETIC ACID AMIDES WITH ANTITUMOR ACTIVITY

(75) Inventors: Ernesto Menta, Monza (IT); Nicoletta Pescalli, Monza (IT)

(73) Assignee: Novuspharma S.p.A., Milan (IT)

( * ) Notice: Subject to any disclaimer, the term of this patent is extended or adjusted under 35 U.S.C. 154(b) by 306 days.

(21) Appl. No.: 10/333,754

(22) PCT Filed: Jul. 12, 2001

(86) PCT No.: PCT/EP01/08075

§ 371 (c)(1),
(2), (4) Date: Jul. 10, 2003

(87) PCT Pub. No.: WO02/08225

PCT Pub. Date: Jan. 31, 2002

(65) Prior Publication Data

US 2004/0029858 A1 Feb. 12, 2004

(30) Foreign Application Priority Data

Jul. 25, 2000 (IT) .......................... MI2000A1697

(51) Int. Cl.
*A61K 31/404* (2006.01)
*C07D 209/04* (2006.01)
(52) U.S. Cl. ...................... 514/419; 548/125; 548/131; 548/136; 548/195; 548/215; 548/245; 548/255; 548/262.2; 548/300.1; 548/364.7; 548/465; 546/139; 546/152; 546/159; 544/180; 544/182; 514/415
(58) Field of Classification Search ................ 548/125, 548/131, 136, 195, 215, 245, 255, 262.2, 548/300.1, 364.7, 465; 514/415, 419; 546/152, 546/159, 139; 544/180, 182
See application file for complete search history.

(56) References Cited

U.S. PATENT DOCUMENTS

| | | | |
|---|---|---|---|
| 6,232,327 B1 * | 5/2001 | Nickel et al. | 514/337 |
| 6,693,119 B2 * | 2/2004 | Nickel et al. | 514/339 |
| 6,753,342 B2 * | 6/2004 | Menta et al. | 514/414 |

FOREIGN PATENT DOCUMENTS

| | | |
|---|---|---|
| EP | 0 490 263 A | 6/1992 |
| WO | WO 99 51224 A | 10/1999 |
| WO | WO 99 55696 A | 11/1999 |
| WO | WO 00 67802 A | 11/2000 |
| WO | WO 01 47916 A | 7/2001 |

OTHER PUBLICATIONS

Polymeropoulos, E. E., et al., "A Peptide Binding Site Model for PDE 4 Inhibitors", *Quant. Struct.-Act. Relat.*, vol. 18, No. 6 (1999) pp. 543-547.

* cited by examiner

*Primary Examiner*—Golam M. M. Shameem
(74) *Attorney, Agent, or Firm*—Rothwell, Figg, Ernst & Manbeck, P.C.

(57) ABSTRACT

2-(1H-Indol-3-yl)-2-oxo-acetamide derivatives of formula (I) having antitumor activity in particular against solid tumors, specifically colon and lung tumors.

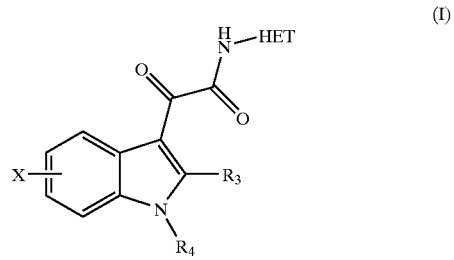

7 Claims, No Drawings

2-(1H-INDOL-3-YL)-2-OXO-ACETIC ACID AMIDES WITH ANTITUMOR ACTIVITY

CROSS REFERENCE TO RELATED APPLICATION

This application is a 35 USC 271 National Phase Entry Application from PCT/EP01/08075, filed Jul. 12, 2001, and designating the U.S.

The present invention relates to 2-(1H-indol-3-yl)-2-oxo-acetamide derivatives having antitumor activity, in particular against solid tumors, specifically colon and lung tumors.

The carcinoma of the colon and rectum is a very common tumor in Western countries, in that it has an incidence of about 421,000 new cases each year in the world and is second only to lung and breast tumors as cause of death.

The percentage of patients which can be treated surgically is about 45–50%, the remaining patients being treated with combined chemotherapy, to obtain a complete remission percentage not above 5%.

Tumors of the colon and rectum are usually refractory or poorly sensitive to chemotherapy available at present and the only effective agent to some extent against this type of cancer is 5-fluorouracil.

Unfortunately no therapeutical alternatives exist at present in case of failure of combined chemotherapy substantially based on 5-FU.

Therefore there is a remarkable need for novel drugs active against this type of tumors.

WO 98/09946 in the name of Asta Medica discloses indole-3-glyoxylamide derivatives. The compounds are substituted at the amido nitrogen atom with aromatic, pyridyl and aryl/heteroaryl substituted pyperazinyl residues and reportedly have antiasthmatic, antiallergic, immunosuppressive and immunomodulating activities. WO 99/51224 in the name of Asta Medica discloses the use of said compounds as antitumor agents as well as novel N-oxides of said products with antitumor activity.

It has now been found that 2-(1H-indol-3-yl)-2-oxo-acetic acid amides with heterocyclic amines have marked antitumor activity, particularly against human solid tumors.

The compounds of the invention can be represented by the general formula (I):

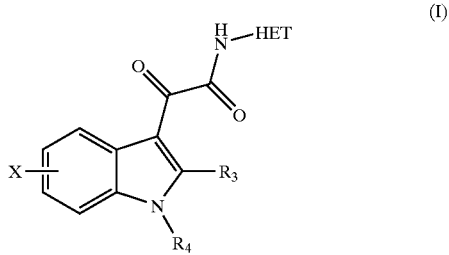

(I)

wherein:
HET is a four to seven membered heterocyclic group, aromatic or non aromatic, containing one or more nitrogen, oxygen or sulfur atoms in one or more heterocyclic rings and optionally substituted on the carbon atoms with halogens, alkyl, hydroxy, alkoxycarbonyl, carboxy, cyano groups or, on the nitrogen atoms, with alkyl, aryl, arylalkyl groups or with oxygen atoms to form N-oxides;

and optionally fused to one or two aryl or cycloalkyl groups, in their turn optionally substituted with halogens, alkyl, hydroxy, alkoxycarbonyl, carboxy, cyano groups;

$R_3$ is hydrogen, $C_1$–$C_4$ alkyl, aralkyl, optionally substituted phenyl;

$R_4$ is straight or branched $C_1$–$C_8$ alkyl, $C_5$–$C_6$ cycloalkyl; aralkyl; heteroaralkyl;

X represents one or more groups, up to four, independently selected from hydrogen, $C_1$–$C_6$ alkyl, hydroxy, $C_1$–$C_4$ alkoxy, $C_1$–$C_3$ haloalkoxy, phenoxy, aralkoxy, $C_1$–$C_3$ acyloxy, amino, $C_1$–$C_3$ alkylamino, $C_1$–$C_3$-acylamino, $C_1$–$C_3$-alkylsulfonylamino, aroylamino, halogen, nitro, cyano, trifluoromethyl, carboxy, $C_1$–$C_3$ alkoxycarbonyl, a $R_aR_bN(CH_2)nC(=O)$— group where $R_a$ and $R_b$ are independently hydrogen, $C_1$–$C_3$-alkyl or $R_a$ and $R_b$ together with the nitrogen atom they are linked to form a pyrrolidino, piperidino, piperazino or morpholino ring and n=0 or an integer 2 to 4, sulfonyl, mercapto, $C_1$–$C_4$-alkylthio, $C_1$–$C_4$-alkylsulfonyl, $C_1$–$C_4$-alkylsulfinyl, aminosulfonyl, $C_1$–$C_3$-alkylaminosulfonyl;

with the proviso that HET is different from aryl/heteroaryl substituted piperazine, or pyridine or pyridine-N-oxide.

The invention also relates to the salts of compounds of formula (I) obtainable by reacting non toxic acids or bases with the ionizable groups present in the compounds (I), and the tautomeric mixtures of the compounds of formula (I).

Examples of four to seven membered heterocyclic rings containing one or more nitrogen, oxygen or sulfur atoms are: pyrrole, furan, thiophene, pyrazole, thiazole, indole, oxazole, imidazole, isothiazole, isoxazole, 1,2,3-triazole, 1,2,4-triazole, 1,2,4-oxadiazole, 1,3,4-oxadiazole, 1,2,5-oxadiazole, 1,2,5-thiadiazole, (1,3,4-thiadiazole, tetrazole, pyrimidine, pyridazine, pyrazine, 1,2,4-triazine, benzofuran, indazole, carbazole, benzoxazole, benzimidazole, benzothiazole, benzotriazole, quinoline, isoquinoline, cinnoline, quinoxaline, quinazoline, phthalazine, 1,2,3-triazine, 1,2,4-triazine, 1,3,5-triazine, purine, pteridine.

Optionally substituted phenyl preferably means phenyl, 4-methylphenyl, 2,4-dimethoxy-phenyl, 4-methoxy-phenyl, 4-nitro-phenyl, 3-chlorophenyl, 4-hydroxyphenyl, 3,5-dimethoxy-4-hydroxy-phenyl, 3-cyano-phenyl, 2-hydroxyphenyl, 2-carboxyphenyl.

Aralkyl preferably means benzyl, phenethyl, naphthylmethyl, biphenylmethyl, optionally substituted with one or more halogens, trifluoromethyl, nitro, cyano, methylsulfonyl, tert-butyl groups.

Heteroaralkyl preferably means pyridylmethyl.

HET is preferably a five or six membered heterocyclic ring selected from the group consisting of furan, pyrrole, thiophene, oxazole, isoxazole, thiazole, isothiazole, pyrazole, imidazole, 1,2,3-triazole, 1,2,4-triazole, 1,3,5-triazole, 1,3,4-oxadiazole, 1,2,4-oxadiazole, 1,2,5-oxadiazole, 1,2,5-thiadiazole, thiadiazole, 1,3,5-thiadiazole, 1,2,3-triazine, 1,2,4-triazine, tetrazole, pyrimidine, pyrazine, pyridazine. Particularly preferred are pyrazole, isoxazole, thiazole, 1,3,5-thiadiazole.

$R_3$ is preferably hydrogen or methyl.

$R_4$ is preferably methyl; benzyl substituted on the benzene ring with one or more groups selected from methyl, fluorine, chlorine, bromine, hydroxy, acetoxy, methoxy, methoxycarbonyl, ethoxycarbonyl, trifluoromethoxy, trifluoromethyl, cyano, nitro, amino, acetylamino, methylsulfonylamino, methylmercapto, methylsulfinyl, methylsulfonyl, phenyl; α-naphthylmethyl, β-naphthylmethyl; 4-pyridylmethyl; 4-pyridylmethyl-N oxide.

X is preferably methyl, ethyl, fluorine, chlorine, bromine, hydroxy, acetoxy, methoxy, phenoxy, trifluoromethoxy, trifluoromethyl, cyano, nitro, amino, acetylamino, methylsulfonylamino, methylmercapto, methysulfinyl, methylsulfonyl.

The compounds of the invention can be prepared by reacting the compounds of formula (II)

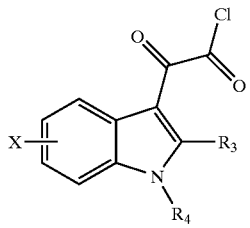
(II)

in which $R_3$, and $R_4$ and X are as defined above, with a compound of formula (III)

H₂N-HET     (III)

in which HET is as defined above.

The reaction is carried out in a solvent such as ethyl ether, isopropyl ether, methyl-tert-butyl ether, tetrahydrofuran, dioxane, 1,2-dimethoxyethane, dichloromethane, 1,2-dichloroethane, toluene, dimethylformamide, dimethylacetamide, dimethylsulfoxide, at a temperature ranging from 0° C. to the reflux temperature of the solvent, and using 1 to 3 molar equivalents of compounds of formula (III), optionally operating in the presence of at least one molar equivalent of an acid-binding agent such as a tertiary organic base, for example triethylamine or diisopropylethylamine, or in the presence of an inorganic base such as alkali or alkaline-earth metal carbonates or bicarbonates.

The reaction is preferably carried out in an ether solvent such as ethyl ether, THF, 1,2-dimethoxyethane, at a temperature ranging from room temperature to 80° C., in the presence of potassium carbonate.

The resulting compounds of formula (I) can subsequently be transformed into other compounds of formula (I) according to the procedures conventionally used for the transformation of functional groups, such as reactions of hydrolysis of ester groups, esterifications of carboxylic acids, amidations and the like. For example, when in compounds of formula (II) the groups X and $R_4$ contain substituents which interfere with the reaction of the compounds of formula (II) with the compounds of formula (III), suitable protective groups will be used, which will be subsequently removed according to conventional methods.

Compounds of formula (II) are obtained by reacting the compounds of formula (IV)

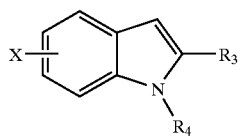
(IV)

in which X, $R_3$ and $R_4$ are as defined above, with oxalyl chloride.

The reaction is generally carried out in a solvent such as ethyl ether, isopropyl ether, tert-butyl methyl ether, tetrahydrofuran, dioxane, dichloromethane, at a temperature ranging from −10° C. to 25° C. and using one to two molar equivalents of oxalyl chloride. The reaction is preferably conducted at a temperature from 0° C. to 25° C. in ethyl ether or in tetrahydrofuran, using a slight excess (1.2 molar equivalents) of oxalyl chloride. The reaction is generally completed within 3 hours.

Compounds of formula (IV) are obtained by reacting the indoles of formula (V)

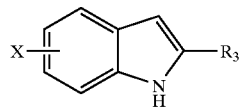
(V)

wherein X and $R_3$ are as defined above, with halides of formula $R_4$-Hal (VI), wherein R4 is as defined above and Hal is preferably chlorine or bromine, in the presence of acid-binding agents.

The reaction is generally carried out using an equimolar amount or a slight excess of halide (VI), in a protic, aprotic dipolar or apolar solvent such as ethanol, isopropanol, tert-butanol, tetrahydrofuran, dioxane, dimethylsulfoxide, dimethylformamide, dimethylacetamide, N-methylpyirrolidinone, acetonitrile, in the presence of an alkali metal or alkaline-earth hydroxide or alkoxide or hydride such as sodium hydroxide, sodium hydride, potassium tert-butoxide. Temperature generally ranges from 0° C. to the reflux temperature of the solvent, for a time ranging from 30′ to 24 hours. The reaction is preferably effected in dimethylsulfoxide in the presence of an equimolar amount of sodium hydride compared with compounds (V), operating at 0–25° C. for the reaction of compounds (V) with sodium hydride, followed by addition of compounds (VI) and heating to 50–70° C. The reaction is generally completed within three hours.

Compounds of formula (V) and (VI) are known or may be prepared with known methods, and many of them are commercially available.

Compounds of formula (III) are known or may be prepared with known methods.

The compounds according to the invention were pharmacologically tested against human tumor cell lines: HT 29 (colon carcinoma), PC 3 (prostate carcinoma), H 460M (lung carcinoma), MKN-45 (gastric carcinoma). Cells were incubated for 144 hour with the tested compound, then cytotoxicity was determined using the MTT test (Mosman, T. "Rapid Colorimetric Assay for Cellular Growth and Survival: Application to Proliferation and Cytotoxicity Assay"; J. Immunolog. Methods, (1983), 65, 66; Green, L. M., "Rapid Colorimetric Assay for Cell Viability; Application to the Quantitation of Cytotoxic and Growth Inhibitory Lymphokines", J. Immunol. Methods, (1984), 70, 257–268).

The obtained data showed that the compounds of the present invention have a marked activity against solid tumors, in particular colon and lung tumors.

The compounds of the invention can be administered in doses ranging from 0.01 mg to 1 g/Kg body weight daily. A preferred administration procedure is that using a dosage from about 1 mg to about 500 mg/Kg body weight daily, using such unitary doses as to administer in 24 hours from about 70 mg to about 3.5 g of the active substance to a patient of about 70 Kg. Such administration procedure can be adjusted to obtain a better therapeutical effect. For example, doses can be adjusted according to the therapeutical conditions of the patient.

The active compounds of the invention can be administered through the oral, intravenous, intramuscular or subcutaneous routes.

The compounds of the invention, when administered, according to well known therapeutical procedures, in combination with other agents used to induce the regression of tumors, synergistically enhance the antitumor effects of said compounds. Examples of the compounds which can be used in combination with the compounds of the invention are cisplatin, carboplatin, doxorubicin, topotecan, taxol, taxotere, vincristine, 5-fluorouracil.

The pharmaceutical compositions of the invention contain therapeutically effective amounts of at least one compound of the invention in mixture with excipients compatible with the pharmaceutical use.

The compositions for the oral route generally comprise an inert diluent or an edible carrier and can be in the form of gelatin capsules or tablets. Other possible oral administration forms are capsules, pills, elixirs, suspensions or syrups.

Tablets, pills, capsules and similar compositions can contain the following ingredients (in addition to the active compound): a ligand, such as microcrystalline cellulose, tragacanth or gelatin; a carrier such as starch or lactose; a disintegrant such as alginic acid, primogel, maize starch and the like; a lubricant such as magnesium stearate; a fluidifying agent such as colloidal silicon dioxide; a sweetener such as saccharose or saccharin or a flavoring agent such as mint flavor, methyl salicylate or orange flavor. When the selected composition is in the form of capsules, it also can contain a liquid carrier such as a fat oil. Other compositions can contain various materials, for example coating agents (for tablets and pills) such as sugar or shellac. The material used in the preparation of the compositions should be pharmaceutically pure and not toxic at the used dosages.

For the pharmaceutical compositions for the parenteral administration, the active ingredient can be included in solutions or suspensions, which can further contain the following components: a sterile diluent such as water for injections, saline solution, oil, polyethylene glycol, glycerin, propylene glycol or other synthetic solvents; antibacterials such as benzyl alcohol; antioxidants such as ascorbic acid or sodium bisulfite; chelating agents such as ethylenediaminetetraacetic acid; buffering agents such as acetates, citrates or phosphates and tonicity agents, such as sodium chloride or dextrose. The parenteral preparations can be contained in ampoules, single-dose syringes, glass or plastic vials.

The present invention will be further described by the following examples.

Preparation 1: 1-(2,4,6-trimethylbenzyl)indole

A solution of indole (1.185 g) in dry DMSO (3 ml) is dropped into a suspension of sodium hydride (60% suspension in mineral oil; 0.44 g) in dry DMSO (10 ml). After two hours, the resulting solution is added with a solution of 2,4,6-trimethylbenzyl chloride (1.9 g) in dry DMSO (2 ml) and the reaction mixture is heated at 60° C. for 6 h. After a night at room temperature, the reaction mixture is poured into water (250 ml) and extracted with ethyl acetate, then dried (Na$_2$SO$_4$) The drying agent is filtered off and the solvent is evaporated off under reduced pressure. The resulting residue is purified by column chromatography (silica gel; eluent n-hexane/AcOEt 9/1), to obtain 2.2 g of 1-(2,4, 6-trimethylbenzyl)indole.

m.p. 79–81° C.

Preparation 2: 1-(n-octyl)indole

A solution of indole (1.0 g) in dry DMSO (1 ml) is dropped into a suspension of sodium hydride (60% suspension in mineral oil; 0.37 g) in dry DMSO (20 ml), heating to 60° C. for 1 h. After cooling at room temperature, the resulting solution is added dropwise with a solution of n-octyl bromide (2.82 ml) in dry DMSO (2.8 ml). After a night at room temperature, the reaction mixture is poured into water (200 ml) and extracted with ethyl acetate (2×50 ml). The combined organic phases are washed with a NaCl saturated solution, dried and evaporated to dryness. The resulting residue is purified by column chromatography (silica gel; eluent n-hexane) to obtain 1.86 g of 1-(n-octyl) indole as oil.

Preparation 3: 1-substituted Indoles

Using the procedures described in preparations 1 and 2, the following 1-substituted indoles are prepared starting from the suitable indoles and halides:

1-(4-cyanobenzyl)indole, oil;
1-(4-chlorobenzyl)-5-chloroindole, oil;
1-(4-chlorobenzyl)-6-chloroindole, oil;
1-(4-chlorobenzyl)-2-methylindole, oil;
1-(4-chlorobenzyl)-5-nitroindole, m.p. 135–137° C.;
1-(4-chlorobenzyl)-6-fluoroindole, oil;
1-[4-(methylsulfonyl)benzyl]-5-chloroindole, m.p. 133–135° C.;
1-(4-chlorobenzyl)-5-methoxyindole, oil;
1-(3-chlorobenzyl)indole, oil;
1-(4-fluorobenzyl)indole, oil;
1-(β-naphthylmethyl)indole, m.p. 106–108° C.;
1-(4-biphenylmethyl)indole, m.p. 130–133° C.;
1-(4-methoxybenzyl)indole, oil;
1-benzylindole, oil;
1-(4-chlorobenzyl)indole, oil;
1-methylindole, oil;
5-chloro-1-(4-chlorobenzyl)-2-methylindole;
5-methoxy-1-(4-chlorobenzyl)-2-methylindole;
1-(4-chlorobenzyl)-2,5-dimethylindole;
4-chloro-1-(4-chlorobenzyl)indole;
4-acetoxy-1-(4-chlorobenzyl)indole;
1-(4-chlorobenzyl)-4-methylindole;
1-(4-chlorobenzyl)-5-cyanoindole;
5-bromo-1-(4-chlorobenzyl)indole;
5,6-dimethoxy-1-(4-chlorobenzyl)indole;
5-benzyloxy-1-(4-chlorobenzyl)indole;
1-(4-chlorobenzyl)-5-(methoxycarbonyl)indole;
5-acetylamino-1-(4-chlorobenzyl)indole;
5-methanesulfonylamino-1-(4-chlorobenzyl)indole;
1-(4-chlorobenzyl)-5-methylindole;
1-(4-chlorobenzyl)-6-methylindole;
1-(4-chlorobenzyl)-7-nitroindole;
1-(4-chlorobenzyl)-7-methylindole;
1-(4-chlorobenzyl)-4-methoxyindole;
1-(4-chlorobenzyl)-4-(ethoxycarbonyl)indole;
1-(4-chlorobenzyl)-4-nitroindole;
4-acetylamino-1-(4-chlorobenzyl)indole;
6-cyano-1-(4-chlorobenzyl)indole;
5,7-dimethoxy-1-(4-chlorobenzyl)indole;
1-(4-chlorobenzyl)-2-phenylindole;
1-(4-chlorobenzyl)-2-phenyl-5-methylindole;
1-(4-chlorobenzyl)-2,7-dimethylindole;
1-(4-chlorobenzyl)-6-methoxyindole;
2-(4-chlorophenyl)-1-ethylindole;
5-benzyloxy-1-(4-chlorobenzyl)-6-methoxyindole;
7-benzyloxy-1-(4-chlorobenzyl)indole;
5-benzyloxy-1-(4-chlorobenzyl)-6-methoxyindole;
1-(4-chlorobenzyl)-5, 6-methylenedioxyindole;
1-(4-chlorobenzyl)-2-(4-chlorophenyl)indole;
4-benzyloxy-1-(4-chlorobenzyl)indole;
1-(4-chlorobenzyl)-7-methoxyindole;
1-(4-chlorobenzyl)-4, 5, 6-trimethoxyindole;
1-(4-chlorobenzyl)-2-ethylindole;
1-(4-chlorobenzyl)-6-nitroindole;
6-benzyloxy-1-(4-chlorobenzyl)indole;
4-fluoro-1-(4-chlorobenzyl)indole;
1-(4-chlorobenzyl)-2-(4-fluorophenyl)indole;
1-(4-chlorobenzyl)-2-(3-chloro-4-fluorophenyl)indole;
1-(4-chlorobenzyl)-2-(3,4-difluorophenyl)indole;

5-acetylamino-1-(4-chlorobenzyl)indole;
1-(4-chlorobenzyl)-2-methyl-5-nitroindole;
1-(4-chlorobenzyl)-2-(4-fluorophenyl)indole;
2-(2-acetylaminophenyl)-1-(4-chlorobenzyl)indole;
1-(4-chlorobenzyl)-7-ethylindole;
6-acetoxy-1-(4-chlorobenzyl)indole;
1-(4-chlorobenzyl)-4,7-dimethoxyindole;
1-(4-chlorobenzyl)-4-methoxycarbonylindole;
4-(4-chlorobenzoylamino)-1-(4-chlorobenzyl)indole;
1-(4-chlorobenzyl)-6-methoxycarbonylindole;
1-(4-chlorobenzyl)-7-methoxycarbonylindole;
1-(4-chlorobenzyl)-6-(2-dimethylaminoethylaminocarbonyl)indole;
1-(4-chlorobenzyl)-5-iodoindole;
1-(n-butyl)indole;
1-(4-chlorobenzyl)-4,5,6,7-tetrafluoroindole;
1-(4-chlorobenzyl)-6-trifluoromethylindole;
4-chloro-1-(4-chlorobenzyl)-6-methoxyindole;
6-chloro-1-(4-chlorobenzyl)-4-methoxyindole;
1-(4-chlorobenzyl)-5-phenoxyindole;
1-(4-chlorobenzyl)-2-(2-chlorophenyl)indole;
1-(4-chlorobenzyl)-5,6-methylenedioxyindole;
1-(2-bromobenzyl)indole;
1-(3-bromobenzyl)indole;
1-(4-bromobenzyl)indole;
1-(4-bromobenzyl)-6-methylindole;
1-(2-methylbenzyl)indole;
1-(3-methylbenzyl)indole;
1-(4-methylbenzyl)indole;
1-(4-methylbenzyl)-6-fluoroindole;
1-(4-tert-butylbenzyl)indole;
1-(4-tert-butylbenzyl)-6-methoxyindole;
1-(2,3,4,5,5-pentafluorobenzyl)indole;
1-(2-fluorobenzyl)indole;
1-(2,6-difluorobenzyl)indole;
1-(3-fluorobenzyl)indole;
1-(3-fluorobenzyl)-5-bromoindole;
1-(4-fluorobenzyl)indole;
1-(3-trifluoromethylbenzyl)-6-nitroindole;
1-(4-trifluoromethylbenzyl)indole;
1-(4-trifluoromethylbenzyl)-5-methanesulfonylaminoindole;
1-(2-chlorobenzyl)indole;
1-(2,6-dichlorobenzyl)indole;
1-(3-chlorobenzyl)indole;
1-(2-cyanobenzyl)indole;
1-(3-cyanobenzyl)indole;
1-(4-cyanobenzyl)-6-fluoroindole;
1-(4-methoxycarbonylbenzyl)indole;
1-(4-methoxycarbonylbenzyl)-6-fluoroindole;
1-(2-nitrobenzyl)indole;
1-(3-nitrobenzyl)indole;
1-(2-methoxy-5-nitrobenzyl)indole;
1-(4-nitrobenzyl)indole;
1-(3,4-difluorobenzyl)indole;
1-(3,4-difluorobenzyl)-6-methoxyindole;
1-(2,5-difluorobenzyl)indole;
1-(3,5-bis(trifluoromethyl)benzyl)indole;
1-(3,5-difluorobenzyl)indole;
1-(2,4-bis(trifluoromethyl)benzyl)indole;
1-(4-(methoxycarbonylmethyl)benzyl)indole;
1-(2,4-difluorobenzyl)indole;
1-(3,5-dimethylbenzyl)indole;
1-(2-trifluoromethylbenzyl)indole;
1-(2-chloro-6-fluorobenzyl)indole;
1-(3,4-dichlorobenzyl)indole;
1-(3,4-dichlorobenzyl)-6-fluoroindole;
1-(3,4-dichlorobenzyl)-6-methylindole;
1-(2-bromo-5-fluorobenzyl)indole;
1-(2-fluoro-3-methylbenzyl)indole;
1-(2,3-difluorobenzyl)indole;
1-(3-chloro-2-fluorobenzyl)indole;
1-(3-(methoxycarbonyl)benzyl)indole;
1-(3,5-dibromobenzyl)indole;
1-(4-fluoro-2-(trifluoromethyl)benzyl)indole;
1-(2,3,6-trifluorobenzyl)indole;
1-(2,4,5-trifluorobenzyl)indole;
1-(2,4, 6-trifluorobenzyl)indole;
1-(2,3,4-trifluorobenzyl)indole;
1-(4-trifluoromethoxybenzyl)indole;
1-(4-trifluoromethoxybenzyl)-6-carbomethoxyindole;
1-(3-trifluoromethoxybenzyl)indole;
1-(2-biphenylmethyl)indole;
1-(4-difluoromethoxybenzyl)indole;
1-(3,4-dimethoxy-6-nitrobenzyl)indole;
1-(3-methoxybenzyl)indole;
1-(2-chloro-4-fluorobenzyl)indole;
1-(2,5-dichlorobenzyl)indole;
1-(4-fluorobenzyl)-4-chloroindole;
1-(4-fluorobenzyl)-5-chloroindole;
1-(4-fluorobenzyl)-6-chloroindole;
1-(4-fluorobenzyl)-2-methylindole;
1-(4-fluorobenzyl)-5-nitroindole;
1-(4-fluorobenzyl)-6-fluoroindole;
1-[4-fluorobenzyl]-5-chloroindole;
1-(4-fluorobenzyl)-5-methoxyindole;
1-(4-fluorobenzyl)-4-methylindole;
1-(4-fluorobenzyl)-5-methylindole;
1-(4-fluorobenzyl)-6-methylindole;
1-(4-fluorobenzyl)-7-methylindole;
1-(4-fluorobenzyl)-5,6-methylenedioxyindole;
1-(3-chlorobenzyl)-5-cyanoindole;
1-(4-biphenylmethyl)-6-carbomethoxyindole;
1-(4-methoxybenzyl)-4-chloroindole;
5-acetylamino-1-benzylindole;
6-fluoro-1-[(4-methylsulfonyl)benzyl]indole;
1-methyl-6-methoxyindole;
5-chloro-1-(4-methoxybenzyl)-2-methylindole;
1-(4-pyridylmethyl)indole;
1-(4-pyridylmethyl)-6-chloroindole.

Preparation 4: 2-(1-(4-chlorobenzyl)-1H-indol-3-yl)-2-oxo-acetyl Chloride

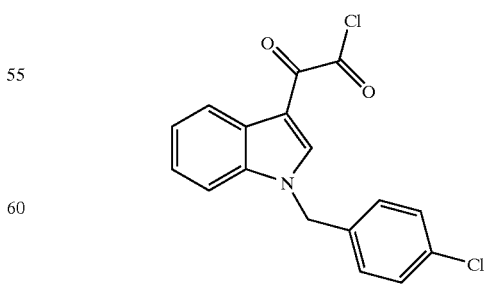

A solution of 1-(4-chlorobenzyl)-1H-indole (2.0 g) in dry ethyl ether (5 ml) kept under stirring and cooled at 0° C. is dropwise added with a solution of oxalyl chloride (0.85 ml)

in dry ethyl ether (2 ml). After completion of the addition, the mixture is left at room temperature for 2h. The separated solid is recovered by filtration, washed with dry ethyl ether and dried under vacuum at 40° C. to give 2-(1-(4-chlorobenzyl)-1H-indol-3-yl)-2-oxo-acetyl chloride (1.64 g).

m.p. 151–153° C.

$^1$H-NMR (CHCl$_3$-d3, ppm): 5.43 (s, 2H); 7.12 (d, 2H); 7.25–7.45 (m, 5H); 8.25 (s, 1H); 8.43 (m, 1H).

The following products were prepared analogously:

2-(1-(4-fluorobenzyl)-1H-indol-3-yl)-2-oxo-acetyl chloride;
2-(1-(3-fluorobenzyl)-1H-indol-3-yl)-2-oxo-acetyl chloride;
2-(1-(2-fluorobenzyl)-1H-indol-3-yl)-2-oxo-acetyl chloride;
2-(1-(4-bromobenzyl)-1H-indol-3-yl)-2-oxo-acetyl chloride;
2-(1-(4-cyanobenzyl)-1H-indol-3-yl)-2-oxo-acetyl chloride;
2-(1-(3-nitrobenzyl)-1H-indol-3-yl)-2-oxo-acetyl chloride;
2-(1-(3,4-difluorobenzyl)-1H-indol-3-yl)-2-oxo-acetyl chloride;
2-(1-benzyl-1H-indol-3-yl)-2-oxo-acetyl chloride.

EXAMPLE 1

N-(1,3,4-thiadiazol-2-yl)-2-(1-(4-fluorobenzyl)-1H-indol-3-yl)-2-oxo-acetamide

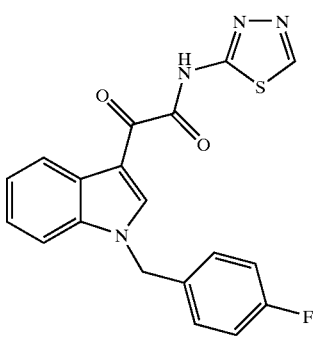

A solution of 2-(1-(4-fluorobenzyl)-1H-indol-3-yl)-2-oxo-acetyl chloride (318 mg) in dry 1,2-dimethoxyethane (5 ml) is added dropwise to a suspension of 2-amino-1,3,4-thiadiazole (91 mg) and dry, ground K$_2$CO$_3$ (138 mg) in 5 ml of 1,2-dimethoxyethane, operating at room temperature. The reaction mixture is left under stirring for 12 hours then poured into water (60 ml). The resulting suspension is stirred for 30 minutes. The precipitate is filtered off and suspended in methanol (10 ml) under stirring for 30 minutes. The solid is recovered by filtration and dried to give N-(1,3,4-thiadiazol-2-yl)-2-(1-(4-fluorobenzyl)-1H-indol-3-yl)-2-oxo-acetamide (168 mg).

m.p. 218–220° C.

$^1$H-NMR (DMSO-d6, ppm): 5.65 (s, 2H); 7.10–7.25 (m, 2H); 7.25–7.50 (m, 4H); 7.65 (m, 1H); 8.25 (m, 1H); 8.95 (s, 1H); 9.35 (s, 1H); 13.30 (br s, 1H).

Elemental Analysis

% calculated for C19H13FN4O2S:
C=59.99, H=3.44, N=14.73, F=4.99
% found:
C=59.96, H=3.52, N=14.45, F=4.85.

EXAMPLE 2

N-(thiazol-2-yl)-2-(1-(4-fluorobenzyl)-1H-indol-3-yl)-2-oxo-acetamide

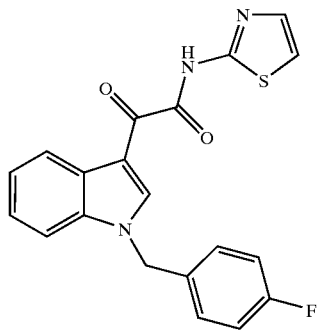

A solution of 1-(4-fluorobenzyl)indole (0.30 g) in ethyl ether (5 ml) is added dropwise with a solution of oxalyl chloride (0.177 ml) in ethyl ether (10 ml). After one hour the reaction mixture is evaporated to dryness and the residue is taken up into 1,2-dimethoxyethane (20 ml). The solution is added with dry, ground K$_2$CO$_3$ (0.183 g), then with 2-aminothiazole (0.119 g). The reaction mixture is stirred at room temperature for 2 hours, then poured into water (100 ml) and stirred for a further hour. The separated solid is recovered by filtration and suspended for an hour under stirring in methanol (10 ml). The product is filtered off and dried to give N-(thiazol-2-yl)-2-(1-(4-fluorobenzyl)-1H-indol-3-yl)-2-oxo-acetamide (0.36 g).

m.p. 233–237° C.

$^1$H-NMR (DMSO-d6, ppm): 5.62 (s, 2H); 7.10–7.25 (m, 2H); 7.25–7.45 (m, 5H); 7.60 (2m, 2H); 8.28 (m, 1H); 8.97 (s, 1H); 12.70 (br s, 1H).

Elemental Analysis

% calculated for C$_{20}$H$_{14}$FN$_3$O$_2$S:
C=63.31, H=3.72, N=11.08, F=5.00, S=8.45
% found:
C=63.21, H=3.70. N=10.81, F=4.86, S=8.20.

EXAMPLE 3

Using the procedures described in examples 1 and 2 and the suitable 1-substituted indoles of preparations 1–3 or (1H-indol-3-yl)-2-oxo-acetyl chlorides of preparation 4 as starting materials, the following products were prepared:

2-(1-(4-fluorobenzyl)-1H-indol-3-yl)-N-(isoxazol-3-yl)-2-oxo-acetamide

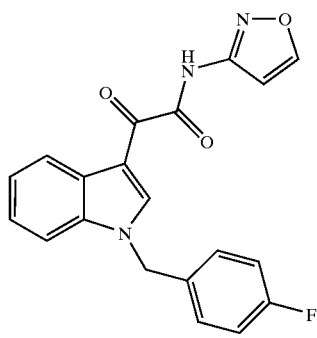

m.p. 180–183° C.  
¹H-NMR (DMSO-d6, ppm): 5.60 (s, 2H); 7.00 (m, 1H), 7.10–7.25 (m, 2H); 7.25–7.45 (m, 4H); 7.65 (m, 1H); 8.25 (m, 1H); 8.90 (m, 1H), 8.97 (s, 1H); 11.65 (brs, 1H).

Elemental Analysis  
% calculated for $C_{20}H_{14}FN_3O_3$:  
C=66.11, H=3.88, N=11.56, F=5.22  
% found:  
C=65.77, H=4,00. N=11.34, F=5.10.

2-[1-(4-fluorobenzyl)-1H-indol-3-yl]-2-oxo-N-(1H-tetrazol-5-yl)-acetamide

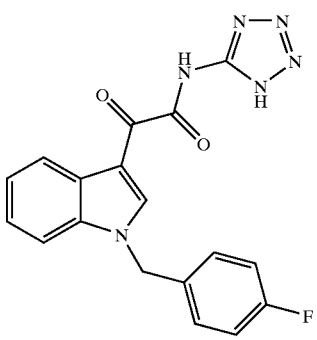

m.p. >270° C.  
¹H-NMR (DMSO-d6, ppm): 5.60 (s, 2H); 7.10–7.25 (m, 2H); 7.25–7.48 (m, 4H); 7.65 (m, 1H); 8.25 (m, 1H); 8.90 (s, 1H); 12.60 (br s, 1H).

Elemental Analysis:  
% calculated for $C_{18}H_{13}FN_6O_2$:  
C=59.34, H=3.60. F=5.21, N=23.07  
% found:  
C=59.12, H=3.64, F=5.12, N=22.59

2-[1-(4-fluoro-benzyl)-1H-indol-3-yl]-2-oxo-N-[4H-(1,2,4)triazol-3-yl]-acetamide

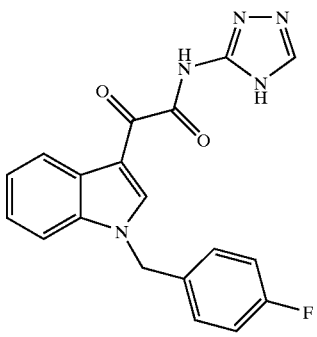

m.p. >270° C.  
Elemental Analysis:  
% calculated for $C_{19}H_{14}FN_5O_2$:  
C=62.81, H=3.88, N=19.27  
% found:  
C=62.50. H=3.94, N=18.78.

2-[1-(4-fluorobenzyl)-1H-indol-3-yl]-2-oxo-N-(1H-pyrazol-3-yl)-acetamide

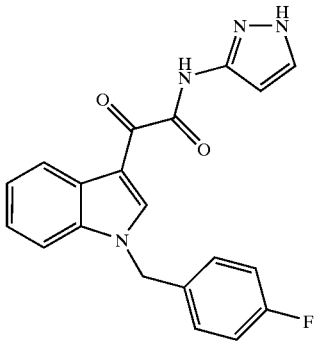

m.p. 210–211° C.  
¹H-NMR (DMSO-d6, ppm): 5.60 (s, 2H); 6.65 (m, 1H); 7.05–7.25 (m, 2H); 7.25–7.48 (m, 4H); 7.60 (m, 1H); 7.75 (m, 1H); 8.98 (s, 1H); 12.75 (br s, 1H); 12.58 (br s, 1H).

N-(4-bromo-5-methyl-2H-pyrazol-3-yl)-2-[1-(4-fluorobenzyl)-1H-indol-3-yl]-2-oxo-acetamide

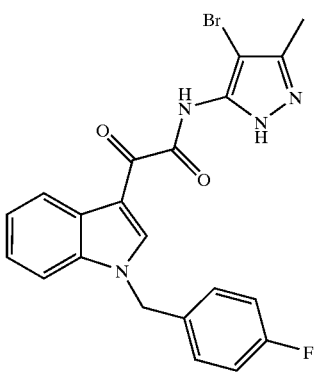

m.p. 198–200° C.;  
1H-NMR (DMSO-d6, ppm): 2.20. (s, 3H); 5.60 (s, 2H); 7.10–7.25 (m, 2H); 7.25–7.45 (m, 4H); 7.65 (m, 1H); 8.30 (m, 1H); 8.80 (s, 1H); 10.40 (br. s, 1H); 12.90 (br. s, 1H).  
% calculated for $C_{21}H_{16}BrFN_4O_2$:  
C=55.40. H=3.54, Br=17.55, N=12.31  
% found:  
C=55.82, H=3.75, Br=17.13, N=12.61.

N-(3,4-Dimethylisoxazol-5-yl)-2-[1-(4-fluorobenzyl)-1H-indol-3-yl]-2-oxoacetamide

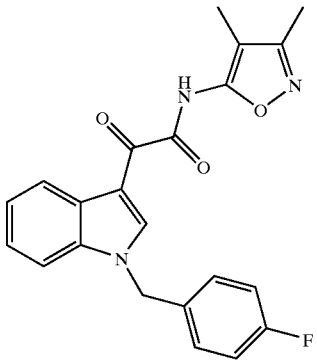

m.p. 159–161° C.
$^1$H-NMR (DMSO-d6, ppm): 1.90 (s, 3H); 2.22, (s, 3H); 5.60 (s, 2H); 7.10–7.25 (m, 2H); 7.25–7.48 (m, 4H); 7.65 (m, 1H); 8.30 (m, 1H); 8.93 (s, 1H); 11.30 (br. s, 1H).
% calculated for $C_{22}H_{18}FN_3O_3$:
C=67.51, H=4.64, F=4.85, N=10.74
% found:
C=67.55, H=4.65, F=4.74, N=10.38.

2-[1-(4-fluorobenzyl)-1H-indol-3-yl]-2-oxo-N-[1,2,4-triazol-4-yl]-acetamide

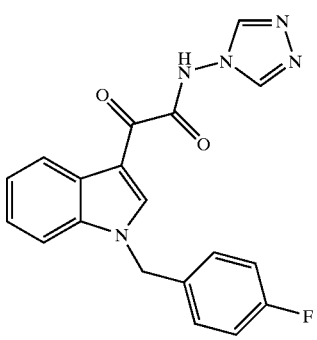

m.p. 210–212° C.
$^1$H-NMR (DMSO-d6, ppm): 5.60 (s, 2H); 7.08–7.20 (m, 2H); 7.25–7.48 (m, 5H); 7.65 (m, 1H); 8.30 (m, 1H); 8.80 (s, 1H); 9.03 (s, 1H); 12.50 (br. s, 1H).
% calculated for $C_{19}H_{14}FN_5O_2$:
C=62.81, H=3.88, F=5.23, N=19.27
% found:
C=62.46, H=4.01, F=4.90. N=18.1.

N-(4,5-dihydrothiazol-2-yl)-2-[1-(4-fluorobenzyl)-1H-indol-3-yl]-2-oxo-acetamide

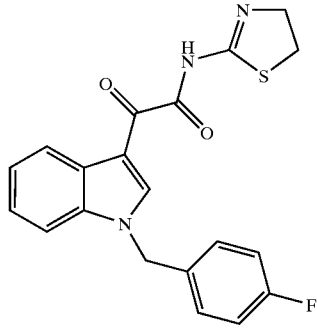

m.p. 200–202° C.
$^1$H-NMR (DMSO-d6, ppm): 3.30 (t, 2H); 3.70 (t, 2H); 5.58 (s, 2H); 7.08–7.45 (m, 6H); 7.60 (m, 1H); 8.25 (m, 1H); 8.55 (s, 1H); 10.20 (br. s, 1H).
% calculated for $C_{20}H_{16}FN_3O_2S$:
C=62.98, H=4.23, F=4.98, N=11.02, S=8.41
% found:
C=62.44, H=4.18, F=4.73, N=11.16, S=8.70.

N-(1,3-dimethyl-1H-pyrazol-5-yl)-2-[1-(4-fluorobenzyl)-1H-indol-3-yl]-2-oxo-acetamide

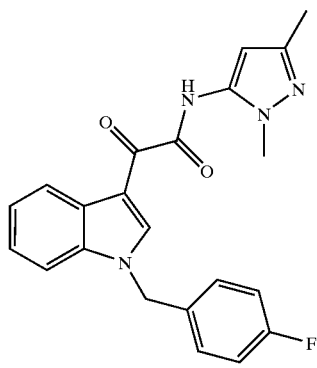

2-[1-(4-fluorobenzyl)-1H-indol-3-yl]-N-(1-methyl-4-oxo-4,5-dihydro-1H-pyrrol-2-yl)-2-oxo-acetamide

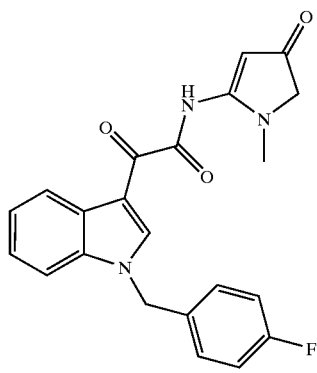

2-[1-(4-fluorobenzyl)-1H-indol-3-yl]-N-(1-methyl-2-oxo-1,2-dihydro-pyrimidin-4-yl)-2-oxo-acetamide

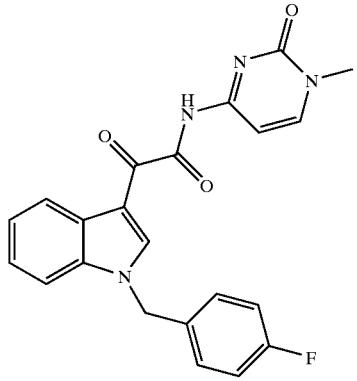

N-(2,6-dioxo-1,2,3,6-tetraidropyrimidin-4-yl)-2-[1-(4-fluorobenzyl)-1H-indol-3-yl]-2-oxo-acetamide

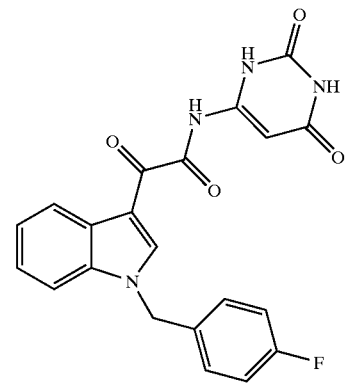

2-[1-(4-fluorobenzyl)-1H-indol-3-yl]-2-oxo-N-(6-oxo-1,6-dihydro-pyrimidin-2-yl)-acetamide

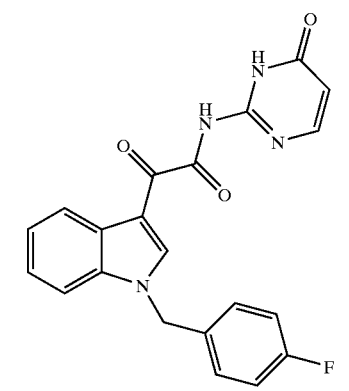

2-[1-(4-Cyanobenzyl)-4-methyl-1H-indol-3-yl]-2-oxo-N-[1,3,4]thiadiazol-2-yl-acetamide

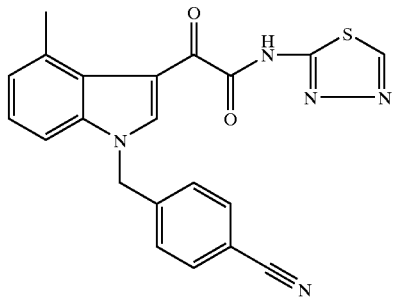

m.p. 203–205° C.
2-[1-(4-chlorobenzyl)-1H-indol-3-yl]-2-oxo-N-(1H-pyrazol-3-yl)-acetamide;
2-[1-(4-fluorobenzyl)-4-methyl-1H-indol-3-yl]-2-oxo-N-(1H-pyrazol-3-yl)-acetamide;
2-[1-(4-chlorobenzyl)-6-fluoro-1H-indol-3-yl]-2-oxo-N-(1H-pyrazol-3-yl)-acetamide;
2-[1-(3-nitrobenzyl)-1H-indol-3-yl]-2-oxo-N-(1H-pyrazol-3-yl)-acetamide;
2-[4-cyano-1-(4-fluorobenzyl)-1H-indol-3-yl]-2-oxo-N-(1H-pyrazol-3-yl)-acetamide;
2-(1-(3,4-difluorobenzyl)-1H-indol-3-yl)-N-(isoxazol-3-yl)-2-oxo-acetamide;
2-(4-methoxycarbonyl-1-(3,4-difluorobenzyl)-1H-indol-3-yl)-N-(isoxazol-3-yl)-2-oxo-acetamide;
2-(6-chloro-1-(3,4-difluorobenzyl)-1H-indol-3-yl)-N-(isoxazol-3-yl)-2-oxo-acetamide;
2-(1-(4-fluorobenzyl)-4-methyl-H-indol-3-yl)-N-(isoxazol-3-yl)-2-oxo-acetamide;
N-(thiazol-2-yl)-2-(1-(4-chlorobenzyl)-1H-indol-3-yl)-2-oxo-acetamide;
N-(thiazol-2-yl)-2-(6-fluoro-1-(4-chlorobenzyl)-1H-indol-3-yl)-2-oxo-acetamide;
N-(thiazol-2-yl)-2-(4-methoxycarbonyl-1-(4-chlorobenzyl)-1H-indol-3-yl)-2-oxo-acetamide;
N-(thiazol-2-yl)-2-(1-(3,4-difluorobenzyl)-1H-indol-3-yl)-2-oxo-acetamide;
N-(thiazol-2-yl)-2-(1-(4-cyanobenzyl)-1H-indol-3-yl)-2-oxo-acetamide;
N-(1,3,4-thiadiazol-2-yl)-2-(1-(4-chlorobenzyl)-1H-indol-3-yl)-2-oxo-acetamide;
N-(1,3,4-thiadiazol-2-yl)-2-(1-(3-fluorobenzyl)-1H-indol-3-yl)-2-oxo-acetamide;
N-(1,3,4-thiadiazol-2-yl)-2-(6-bromo-1-(4-chlorobenzyl)-1H-indol-3-yl)-2-oxo-acetamide;
N-(1,3,4-thiadiazol-2-yl)-2-(1-benzyl-1H-indol-3-yl)-2-oxo-acetamide;
N-(benzimidazol-2-yl)-2-[1-(4-fluorobenzyl)-1H-indol-3-yl]-2-oxo-acetamide;
N-(benzothiazol-2-yl)-2-[1-(4-chlorobenzyl)-1H-indol-3-yl]-2-oxo-acetamide;
N-(benzotriazol-1-yl)-2-[1-(3,4-difluorobenzyl)-1H-indol-3-yl]-2-oxo-acetamide;
N-(5-bromopyrimidin-2-yl)-2-[1-(4-cyanobenzyl)-1H-indol-3-yl]-2-oxo-acetamide;
N-(5-bromothiazol-2-yl)-2-[1-(4-fluorobenzyl)-1H-indol-3-yl]-2-oxo-acetamide;
2-[1-(4-chlorobenzyl)-1H-indol-3-yl]-N-(4-ethoxycarbonylpyrazol-3-yl)-2-oxo-acetamide;
N-(4-cyanopyrazol-3-yl)-2-[1-(4-fluorobenzyl)-1H-indol-3-yl]-2-oxo-acetamide;

2-[1-benzyl-1H-indol-3-yl]-N-(3-cyano-4,5-dimethylfuran-2-yl)-2-oxo-acetamide;
2-[1-(4-bromobenzyl)-1H-indol-3-yl]-N-(4,5-dimethylthiazol-2-yl)-2-oxo-acetamide;
N-(5,6-dimethyl-1,2,4-triazin-2-yl)-2-[1-(3-nitrobenzyl)-1H-indol-3-yl]-2-oxo-acetamide;
N-(1,3-dimethyl-2,4-dihydro-2,4-dioxopyrimidin-6-yl)-2-[4-methyl-1-(4-chlorobenzyl)-1H-indol-3-yl]-2-oxo-acetamide;
N-(1-ethylpyrazol-5-yl)-2-[1-(4-fluorobenzyl)-1H-indol-3-yl]-2-oxo-acetamide;
N-(5-ethyl-1,3,4-thiadiazol-2-yl)-2-[1-(4-methylbenzyl)-1H-indol-3-yl]-2-oxo-acetamide;
N-(5-ethylthio-1,3,4-thiadiazol-2-yl)-2-[1-(4-methoxybenzyl)-1H-indol-3-yl] 2-oxo-acetamide;
N-(5-hydroxypyrazol-3-yl)-2-[1-(4-methoxybenzyl)-1H-indol-3-yl]-2-oxo-acetamide;
N-(imidazol-2-yl)-2-[1-(4-trifluoromethylbenzyl)-1H-indol-3-yl]-2-oxo-acetamide;
2-[1-(3,4-difluorobenzyl)-1H-indol-3-yl]-N-(isoquinolin-1-yl)-2-oxo-acetamide;
N-(4-methoxy-6-methylpyrimidin-2-yl)-2-[1-(4-trifluoromethylbenzyl)-1H-indol-3-yl]-2-oxo-acetamide;
2-[1-(4-chlorobenzyl)-1H-indol-3-yl]-N-(1-methylbenzimidazol-2-yl)-2-oxo-acetamide;
2-[1-(3,4-difluorobenzyl)-1H-indol-3-yl]-N-(3-methylisothiazol-5-yl)-2-oxo-acetamide;
2-[1-(4-methoxybenzyl)-1H-indol-3-yl]-N-(5-methylisoxazol-3-yl)-2-oxo-acetamide;
2-[1-(4-bromobenzyl)-1H-indol-3-yl]-N-(3-methylisoxazol-5-yl)-2-oxo-acetamide;
2-[1-(4-cyanobenzyl)-1H-indol-3-yl]-N-(5-methylipyrazol-3-yl)-2-oxo-acetamide;
2-[1-benzyl-1H-indol-3-yl]-N-(4-methylthiazol-2-yl)-2-oxo-acetamide;
2-[6-fluoro-1-(4-chlorobenzyl)-1H-indol-3-yl]-N-(5-methylthiazol-2-yl)-2-oxo-acetamide;
2-[6-fluoro-1-(4-chlorobenzyl)-1H-indol-3-yl]-N-(5-nitrothiazol-2-yl)-2-oxo-acetamide;
N-(5-phenylpyrazol-3-yl)-2-[4-methyl-1-(4-chlorobenzyl)-1H-indol-3-yl]-2-oxo-acetamide;
N-(5-phenyl-1,3,4-thiadiazol-2-yl)-2-[1-(3-methoxycarbonylbenzyl)-1H-indol3-yl]-2-oxo-acetamide;
N-(4-phenylthiazol-2-yl)-2-[1-(4-chlorobenzyl)-1H-indol-3-yl]-2-oxo-acetamide;
N-(pirazin-2-yl)-2-[1-(4-fluorobenzyl)-1H-indol-3-yl]-2-oxo-acetamide;
N-(4-cyanopyrazol-3-yl)-2-[1-(3,4-dichlorobenzyl)-1H-indol-3-yl]-2-oxo-acetamide;
N-(pyrimidin-2-yl)-2-[1-(4-trifluoromethylbenzyl)-1H-indol-3-yl]-2-oxo-acetamide;
2-[1-(4-chlorobenzyl)-1H-indol-3-yl]-2-oxo-N-(pyrimidin-4-yl)-acetamide;
N-(4-carboxymethylthiazol-2-yl)-2-[1-(4-chlorobenzyl)-1H-indol-3-yl]-2-oxo-acetamide;
2-[1-(4-fluorobenzyl)-H-indol-3-yl]-2-oxo-N-(1,2,4-triazin-3-yl)-acetamide;
N-(5-carboxy-1,2,4-triazol-3-yl)-2-[1-(3-fluorobenzyl)-1H-indol-3-yl]-2-oxo-acetamide;
2-[1-(2-fluorobenzyl)-1H-indol-3-yl]-2-oxo-N-(5-trifluoromethyl-1,3,4-thiadiazol-2-yl)-acetamide.

What is claimed is:
1. Compounds of formula (I)

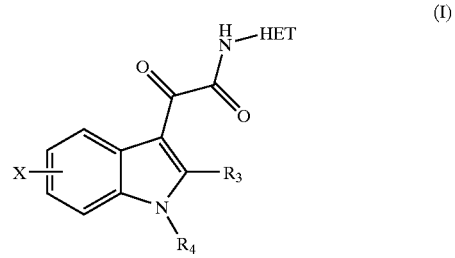

wherein:
HET is a four to seven membered heterocyclic group, aromatic or non aromatic, containing one or more nitrogen, oxygen or sulfur atoms in one or more heterocyclic rings and optionally substituted on the carbon atoms with halogens, alkyl, hydroxy, alkoxycarbonyl, carboxy, cyano groups or, on the nitrogen atoms, with alkyl, aryl, arylalkyl groups or with oxygen atoms to form N-oxides;
and optionally fused to one or two aryl or cycloalkyl groups, in their turn optionally substituted with halogens, alkyl, hydroxy, alkoxycarbonyl, carboxy, cyano groups;
$R_3$ is hydrogen, $C_1$–$C_4$ alkyl, aralkyl, optionally substituted phenyl;
$R_4$ is straight or branched $C_1$–$C_8$ alkyl, $C_5$–$C_6$ cycloalkyl; aralkyl; heteroaralkyl;
X represents one or more groups, up to four, independently selected from hydrogen, $C_1$–$C_6$ alkyl, hydroxy, $C_1$–$C_4$ alkoxy, $C_1$–$C_3$ haloalkoxy, phenoxy, aralkoxy, $C_1$–$C_3$ acyloxy, amino, $C_1$–$C_3$ alkylamino, $C_1$–$C_3$-acylamino, $C_1$–$C_3$-alkylsulfonylamino, aroylamino, halogen, nitro, cyano, trifluoromethyl, carboxy, $C_1$–$C_3$ alkoxycarbonyl, a $R_aR_bN(CH_2)nC(=O)$— group where $R_a$ and $R_b$ are independently hydrogen, $C_1$–$C_3$-alkyl or $R_a$ and $R_b$ together with the nitrogen atom they are linked to form a pyrrolidino, piperidino, piperazino or morpholino ring and n=0 or an integer 2 to 4, sulfonyl, mercapto, $C_1$–$C_4$-alkylthio, $C_1$–$C_4$-alkylsulfonyl, $C_1$–$C_4$-alkylsulfinyl, aminosulfonyl, $C_1$–$C_3$-alkylaminosulfonyl;
with the proviso that HET is different from aryl/heteroaryl substituted piperazine, or pyridine, or pyridine-N-oxide,
and the pharmaceutically acceptable salts and tautomeric mixtures thereof.

2. Compounds as claimed in claim 1 wherein HET is selected from pyrrole, furan, thiophene, pyrazole, thiazole, indole, oxazole, imidazole, isothiazole, isoxazole, 1,2,3-triazole, 1,2,4-triazole, 1,2,4-oxadiazole, 1,3,4-oxadiazole, 1,2,5-oxadiazole, 1,2,5-thiadiazole, 1,3,4-thiadiazole, tetrazole, pyrimidine, pyridazine, pyrazine, 1,2,4-triazine, benzofuran, indazole, carbazole, benzoxazole, benzimidazole, benzothiazole, benzotriazole, quinoline, isoquinoline, cinnoline, quinoxaline, quinazoline, phthalazine, 1,2,3-triazine, 1,2,4-triazine, 1,3,5-triazine, purine, pteridine.

3. Compounds as claimed in claim 2 wherein HET is selected from pyrazole, isoxazole, thiazole, 1,3,5-thiadiazole.

4. Compounds as claimed in claim 1 wherein $R_3$ is hydrogen or methyl.

5. Compounds as claimed in claim 1 wherein $R_4$ is methyl; benzyl substituted on the benzene ring with one or more groups selected from methyl, fluorine, chlorine, bromine, hydroxy, methoxycarbonyl, ethoxycarbonyl, acetoxy, methoxy, trifluoromethoxy, trifluoromethyl, cyano, nitro, amino, acetylamino, methylsulfonylamino, methylmercapto, methylsulfinyl, methylsulfonyl, phenyl; α-naphthylmethyl; β-naphthylmethyl; 4-pyridylmethyl; 4-pyridylmethyl N-oxide.

6. Compounds as claimed in claim 1 wherein X is methyl, ethyl, fluorine, chlorine, bromine, hydroxy, acetoxy, methoxy, phenoxy, trifluoromethoxy, trifluoromethyl, cyano, nitro, amino, acetylamino, methylsulfonylamino, methylmercapto, methysulfinyl, methylsulfonyl.

7. Pharmaceutical compositions containing a compound of claim 1 in mixture with a suitable carrier.

* * * * *